(12) United States Patent
Stamatialis et al.

(10) Patent No.: US 11,806,676 B2
(45) Date of Patent: Nov. 7, 2023

(54) COMPOSITIONS FOR USE IN THE SIMULTANEOUS REMOVAL OF ENDOTOXINS AND UREMIC SOLUTES DURING THE TREATMENT OF PATIENTS

(71) Applicant: Universiteit Twente, Enschede (NL)

(72) Inventors: Dimitrios Stamatialis, Deventer (NL); Ilaria Geremia, Teglio Veneto (IT)

(73) Assignee: Universiteit Twente, Enschede (NL)

( * ) Notice: Subject to any disclaimer, the term of this patent is extended or adjusted under 35 U.S.C. 154(b) by 524 days.

(21) Appl. No.: 17/262,301

(22) PCT Filed: Jul. 25, 2019

(86) PCT No.: PCT/NL2019/050484
§ 371 (c)(1),
(2) Date: Jan. 22, 2021

(87) PCT Pub. No.: WO2020/022894
PCT Pub. Date: Jan. 30, 2020

(65) Prior Publication Data
US 2021/0252462 A1    Aug. 19, 2021

(30) Foreign Application Priority Data

Jul. 25, 2018    (EP) .................................... 18185495

(51) Int. Cl.
*B01D 69/14*    (2006.01)
*B01D 69/02*    (2006.01)
(Continued)

(52) U.S. Cl.
CPC ............ *B01D 69/147* (2013.01); *A61M 1/34* (2013.01); *B01D 69/02* (2013.01); *B01D 71/021* (2013.01);
(Continued)

(58) Field of Classification Search
CPC .. B01D 2325/36; B01D 69/02; B01D 69/147; B01D 71/021; B01D 71/62; B01D 71/68; B01J 20/103; B01J 20/165; B01J 20/20; B01J 20/28026; B01J 20/28038; B01J 20/28085; B01J 20/321; B01J 20/3212; B01J 20/324; A61M 1/1694; A61M 1/1696; A61M 1/34
See application file for complete search history.

(56) References Cited

U.S. PATENT DOCUMENTS 10,625,241 B2 *   4/2020   Baier-Goschütz ... B01J 20/3221
10,702,797 B2 *   7/2020   Ash ..................... B01J 20/28033
(Continued)

OTHER PUBLICATIONS

Nov. 8, 2019—(WO) International Search Report—Appl No. PCT/NL2019/050484.
(Continued)

*Primary Examiner* — Terry K Cecil
(74) *Attorney, Agent, or Firm* — Banner & Witcoff, Ltd.

(57) ABSTRACT

Disclosed are compositions for use in the simultaneous removal of endotoxins from dialysate and uremic solutes from blood during the treatment of patients. The treatment is selected from the group consisting of hemodialysis and hemodiafiltration. The compositions comprise sorbent particles embedded in a membrane comprising a polymer and a hydrophilic additive.

5 Claims, 5 Drawing Sheets

(51) Int. Cl.
- *B01D 71/62* (2006.01)
- *B01D 71/68* (2006.01)
- *A61M 1/34* (2006.01)
- *A61M 1/16* (2006.01)
- *B01D 71/02* (2006.01)
- *B01J 20/20* (2006.01)
- *B01J 20/28* (2006.01)
- *B01J 20/32* (2006.01)

(52) U.S. Cl.
CPC ............ *B01D 71/62* (2013.01); *B01D 71/68* (2013.01); *B01J 20/20* (2013.01); *B01J 20/28026* (2013.01); *B01J 20/28038* (2013.01); *B01J 20/28085* (2013.01); *B01J 20/321* (2013.01); *B01J 20/324* (2013.01); *B01J 20/3212* (2013.01); *A61M 1/1696* (2013.01); *B01D 2325/36* (2013.01)

(56) References Cited

U.S. PATENT DOCUMENTS

| 10,967,115 B2* | 4/2021 | Imaji ................. B01J 20/28071 |
| 2010/0004588 A1 | 1/2010 | Yeh et al. |
| 2015/0290380 A1 | 10/2015 | Welzel et al. |

OTHER PUBLICATIONS

Tijink et al. "Mixed Matrix Membranes: A New Asset for Blood Purification Therapies" Blood Purification, vol. 37, No. 1, Jan. 1, 2014, pp. 1-3.

Pavlenko et al. "New low-flux mixed matrix membranes that offer superior removal of protein-bound toxins from human plasma" Scientific Reports, vol. 6, No. 1, Oct. 5, 2016, pp. 1-9.

* cited by examiner

COMPOSITIONS FOR USE IN THE SIMULTANEOUS REMOVAL OF ENDOTOXINS AND UREMIC SOLUTES DURING THE TREATMENT OF PATIENTS

RELATED APPLICATION DATA

This application is a National Stage Application under 35 U.S.C. 371 of co-pending PCT application number PCT/NL2019/050484 designating the United States and filed Jul. 25, 2019; which claims the benefit of EP application number 18185495.1 and filed Jul. 25, 2018 each of which are hereby incorporated by reference in their entireties.

FIELD OF THE INVENTION

The invention disclosed herein relates to compositions comprising sorbent particles embedded in a membrane matrix for use in the simultaneous removal of endotoxins from dialysate and uremic solutes from blood during the treatment of patients.

BACKGROUND

Hemodialysis and hemodiafiltration are much used methods to remove uremic solutes from the blood of patients. In the setup of these treatments, blood is flown on one side of a dialysis membrane, while dialysate flows on the other side of the membrane. In hemodialysis, uremic solutes flow through the membrane to the dialysate due to a difference in concentration. In hemodiafiltration, a replacement fluid is added to the blood (before or after the blood has been in contact with the dialysis membrane), and transport of uremic solutes from the blood to the dialysate is based on both diffusion and convection. In a typical hemodialysis or hemodiafiltration therapy, the blood is returned to the patient after it has been in contact with the dialysis membrane.

The dialysate used in hemodialysis or hemodiafiltration has to comply with certain water purity standards. Especially the concentration of endotoxins in the dialysate needs to be below certain standards. It will be understood that endotoxins are to the skilled person synonymous with the terms lipopolysaccharides (LPS) and lipoglycans. Furthermore, it will be understood that the term lipooligosaccharide (LOS) is used to refer to a low-molecular-weight form of bacterial lipopolysaccharides. Endotoxins consist of a hydrophobic moiety, called Lipid A, and a polysaccharide. The polysaccharide comprises regions called the inner core, outer core and O-antigen. Without wishing to be bound by theory, it is believed that endotoxins are mainly encountered in the outer membrane of Gram-negative bacteria.

The concentration of endotoxins is typically given in endotoxin units per milliliter (EU/mL) as described by M. E. Dawson in Associates of Cape Cod, Inc. LAL Update, vol. 15, no. 4, December 1997, pages 2-3. The skilled person is aware that International Units (IU) per milliliter are used as well for the concentration of endotoxins, and that 1 EU/mL equals 1 IU/mL.

It will be understood that the standards for endotoxin concentration in dialysate, and different kinds of dialysis fluid, may differ. One international standard is provided by ISO 23500 from 2011. In Table 4 thereof, it is indicated that the maximum endotoxin levels in standard dialysis fluid, which is considered the minimum acceptable quality for routine hemodialysis, is 0.5 EU/mL. The action level, which is typically the level of endotoxins at which measures need to be taken to prevent any further increase towards the maximum level, is set at 0.25 EU/mL. For ultrapure dialysis fluid, which is the recommended standard for hemodialysis, the maximum allowable level of endotoxins is 0.03 EU/mL. According to paragraph 1.1 of ISO 23500 from 2011, the same standards apply to dialysis fluid for hemodiafiltration.

Another example of standards for endotoxin concentration in dialysate is provided in "*Waterbehandeling voor hemodialyse en online hemo(dia)filtratie—Richtlijn Nederlandse Federatie voor Nefrologie, NfN—watercommissie*" (Offerman et al., 2013, update 2016). This document relates to the standards for water quality in The Netherlands. In Table 6 on page 6 of this document, it is listed that there is no requirement formulated for the endotoxin concentration in tap water. Purified water should contain <0.25 EU/mL of endotoxins. Dialysis fluid for use in hemodialysis should contain <0.25 EU/mL of endotoxins. In Table 7 on page 6 of the same document, the standards of endotoxin concentration are listed for hemodiafiltration. Therein, the requirements are listed as extra purified water that should contain <0.05 EU/mL of endotoxins, and extra purified dialysis fluid that should contain <0.05 EU/mL of endotoxins.

As a consequence of these requirements, fluids to be used as dialysate in hemodialysis or hemodiafiltration need to be purified prior to use. Typically, this requires a large purification machine that may contain multiple filters, which is a disadvantage for the design of portable artificial kidneys. Furthermore, removal of endotoxins from dialysate with special purification machines typically requires large amounts of water. In addition, in a portable artificial kidney the dialysate is preferably reused for at least several cycles.

In another aspect, purified dialysate is not readily available everywhere. For example, in developing countries, purified dialysate may be difficult to distribute, hard to obtain or too expensive for treatment of poor patients.

For at least the above reasons, there is a need for a simpler method to remove endotoxins from dialysate.

In another aspect, it is believed that when removal of uremic solutes from the blood of a patient during hemodialysis or hemodiafiltration solely relies on diffusion and/or convection of the uremic solutes from the blood to the dialysate, this only results in partial removal of uremic solutes from the blood of the patient.

For at least the above reasons, it would be especially advantageous if the step of endotoxin removal from the dialysate is combined with the removal of uremic solutes from the blood of the patient during hemodialysis or hemodiafiltration.

In Chapter 7 of his thesis entitled "*Mixed Matrix Membrane Adsorbers for Protein and Blood Purification*" (Enschede, 2007), Saiful describes endotoxin removal during dialysis by using sorbent particles (strong anion exchange resins or activated carbon particles) embedded in cellulose acetate mixed matrix membranes (MMM). There is, however, no mention of the simultaneous removal of endotoxins from dialysate and uremic solutes from blood.

In the journal *Int. J. Artif. Organs,* 2017, vol. 40, an abstract of an oral presentation is listed on page 388. The abstract pertains to a mixed matrix membrane composed of activated carbon particles embedded into a polyethersulfone and polyvinylpyrrolidone blend for the removal of endotoxins from dialysate in a hemodialysis setup. The abstract is silent about the simultaneous removal of endotoxins from dialysate and uremic solutes from blood.

Pavlenko et al., *Scientific Reports,* vol. 6 article number 34429 describes removal of protein-bound uremic solutes using mixed matrix membrane (activated carbon embedded in MMM based on polyethersulfone and polyvinylpyrrolidone blend), but there is no mention about removal of endotoxins.

Pavlenko et al., *Scientific Reports*, vol. 7, article number 14914, describe carbon-based sorbent particles to which uremic toxins are adsorbed. The sorbent particles in this publication are not embedded in a membrane, nor is there any mention of endotoxins, let alone that endotoxins adsorb to the carbon-based sorbent particles disclosed therein.

It is desired that compositions are developed that address one or more of the abovementioned problems specifically related to the simultaneous removal of endotoxins from dialysate and uremic solutes from blood during the treatment of patients.

SUMMARY OF THE INVENTION

In one aspect, the present invention pertains to compositions comprising sorbent particles for use in the simultaneous removal of endotoxins from dialysate and uremic solutes from blood during the treatment of patients;
  wherein said particles are embedded into a membrane, said membrane comprising at least one polymer selected from the group consisting of polysulfone, polyethersulfone, polyphenylenesulfone, polyarylethersulfone, polyamide, polyetherimide, polyimide, polyethylene-co-vinyl alcohol, polyethylene-co-vinyl acetate, cellulose acetate, cellulose triacetate, polyvinylidene fluoride, polyvinylchloride, polyacrylonitrile, polyurethane, polyether ether ketone, and polyacrylic acid;
  wherein said membrane further comprises at least one hydrophilic additive selected from the group consisting of polyvinylpyrrolidone, polyethylene glycol, dextran, glycerol, diethylene glycol, octanol, oxalic acid, maleic acid, tartaric acid, fumaric acid, lithium chloride, and calcium chloride; wherein said treatment is selected from the group consisting of hemodialysis and hemodiafiltration;
  wherein said dialysate comprises endotoxins at a concentration of at least 0.03 EU/mL at the point in time when the dialysate is first brought into contact with said membrane.

DETAILED DESCRIPTION OF THE INVENTION

Figure 1:
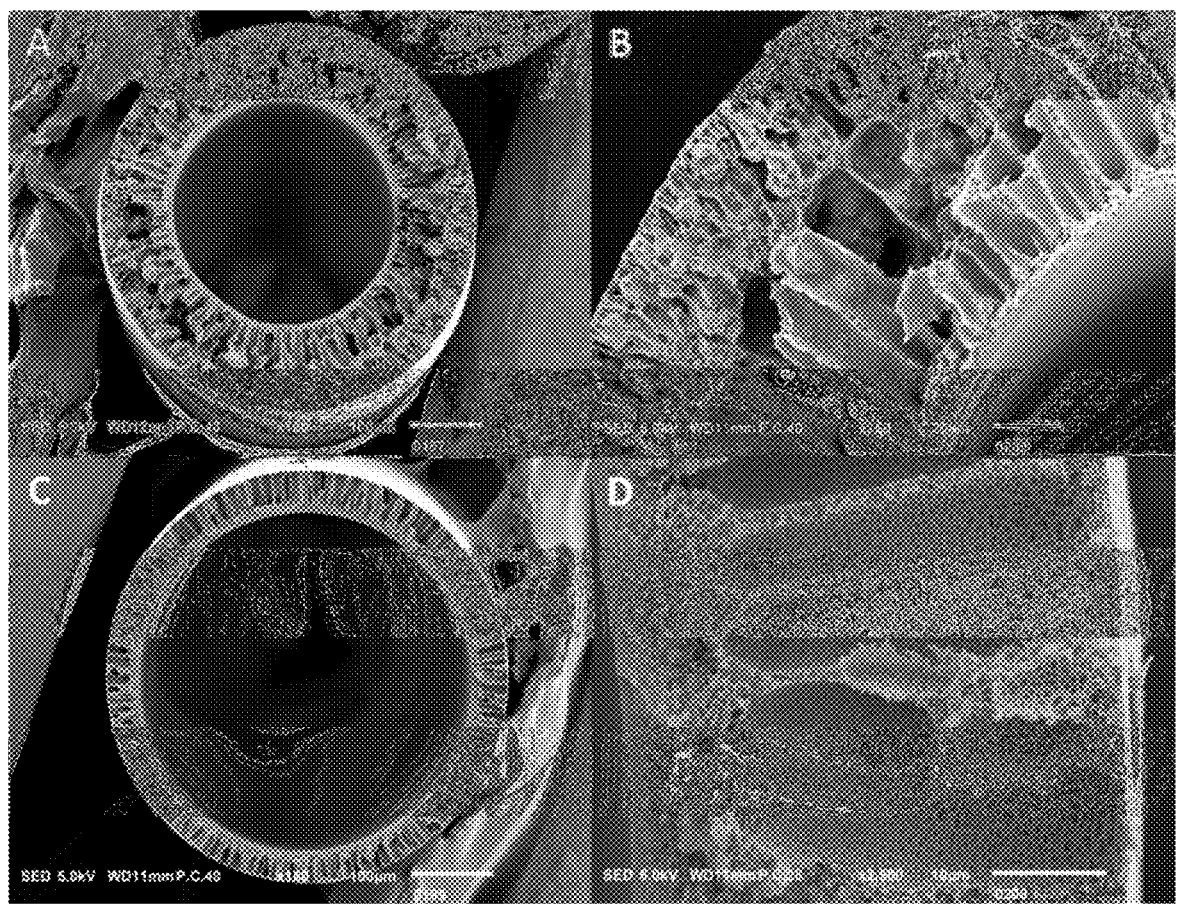
FIG. 1 depicts scanning electron microscopy (SEM) images of the dual layer MMM (panel A: overall cross section, panel B: magnification of the wall) and single layer PES/PVP hollow fibers without particles (panel C: overall cross section, panel D: magnification of the wall).

The invention, in a broad sense, is based on the judicious insight that compositions comprising sorbent particles embedded in a membrane as described herein are suitable to simultaneously remove endotoxins from dialysate and uremic solutes from blood during the treatment of patients, wherein the treatment is selected from the group consisting of hemodialysis and hemodiafiltration.

In one aspect, the compositions of the invention allow dialysate comprising endotoxin levels above the normal standards as described above to be used during the treatment of patients. Thus, removal of endotoxins from water before said water is used as dialysate is not necessary when using the compositions of the inventions. In another aspect, the inventors believe that this prevents the need to connect the dialyzer unit to an additional dialysis fluid purification unit or to bring purified water to places that are difficult to reach. In another aspect, the invention is beneficial for places, for example developing countries, where ultra-pure water and dialysate complying with the standards as described below is not readily available and/or expensive.

In yet another aspect, the inventors believe that the compositions of the invention allow recycling of the dialysate. Thus, the total volume of water required for dialysis treatment of patients is reduced. Furthermore, costs for dialysis treatment are reduced.

In still another aspect, the composition of the invention provides a safe barrier preventing the flow of endotoxins from the dialysate to the blood of the patient.

In another aspect, it is advantageous that the composition of the invention for use in the simultaneous removal of endotoxins from dialysate and uremic solutes from the blood of patients, reduces the number of membranes required in hemodialysis and hemodiafiltration, as normally several membranes are used to remove endotoxins from dialysate and an additional membrane is used to remove uremic solutes and other waste products from the blood of patients.

In yet another aspect, it is advantageous that the composition of the invention is recyclable, as the sorbent particles, particularly ion exchange resins, can be regenerated after use.

Without wishing to be bound by theory, it is believed that the endotoxins from the dialysate are adsorbed to the sorbent particles that are comprised in compositions of the invention. Again without wishing to be bound by theory, it is believed that the uremic solutes from the blood are removed from the blood mainly by adsorption to the sorbent particles that are comprised in compositions of the invention and possibly to a minor extent by transport to the dialysate. Still without wishing to be bound by theory, it is believed that adsorption of molecules to the sorbent particles occurs via hydrophobic interaction or electrostatic interactions and/or hydrogen bonding.

Sorbent particles are defined herein as particles to which small, middle-size and large molecules can adsorb. In particular, sorbent particles as disclosed herein are particles to which uremic solutes and endotoxins adsorb.

In preferred embodiments, the sorbent particles are selected from the group consisting of activated carbon particles, ion exchange resins, unmodified silica particles, $C_2$-derivitised silica particles, $C_4$-derivitsed silica particles, $C_6$-derivitsed silica particles, $C_8$-derivitsed silica particles, $C_{16}$-derivitsed silica particles, ion exchange silica particles, zeolites, ceramic particles, porous polymeric particles, non-porous polymeric particles, molecular imprinted particles, and combinations thereof. Herein, it will be understood that ion exchange resins may be weak or strong cation exchange resins or weak or strong anion exchange resins.

In preferred embodiments, the sorbent particles are activated carbon particles. Activated carbon particles preferably have an average pore size in a range of from 0.1 to 20 nm, most preferably from 1 to 5 nm. In another aspect, activated carbon particles preferably have a size in a range of from 0.1 to 100 μm, preferably in a range of from 0.1 to 30 μm, most preferably the activated carbon particles are smaller than 25 μm.

In some embodiments, activated carbon particles have a Brunauer-Emmet-Teller (BET) surface area from 100 to 10,000 squared meters per gram ($m^2/g$), most preferably 2000 $m^2/g$.

Activated carbon particles are optionally impregnated with at least one inorganic impregnate selected from the group consisting of iodine, silver, aluminum, manganese, zinc, iron, lithium, and calcium. Preferably, aluminum, manganese, zinc, iron, lithium, and calcium are in their cationic form.

Activated carbon particles are preferably selected from the group consisting of AC Norit A Supra particles and CMK3 particles.

In preferred embodiments, the sorbent particles have a regular, in particular spherical, or an irregular shape. The sorbent particles may applied as shards, fibers, powders, or a combination thereof. Powders include, but are not limited to, metal powders, plastic powders, normal phase silica, fumed silica and activated carbon.

It is understood that the suitable amount of sorbent particles in the mixture that is to be extruded depends on the type of polymer and the concentration of the polymer that is used. In general, the amount of sorbent particles in the mixture that is to be extruded may vary between 1 and 95% by weight as compared to the total weight of the mixture. In preferred embodiments, the amount of sorbent particles in the mixture to extruded varies within a range of from 1 to 70% by weight, preferably more than 5% by weight, most preferably in a range of from 10 to 60% by weight.

The membranes of the invention are preferably mixed matrix membranes, and even more preferably dual layer mixed matrix membranes. The membranes of the invention may be asymmetric or symmetric. In some embodiments, the sorbent particles, in particular activated carbon particles, are present in the layer of the dual layer mixed matrix membrane that is closest to the dialysate. Typically, this layer is the outer layer of the dual layer mixed matrix membrane. Without wishing to be bound by theory, it is believed that in such a way contact with blood can be minimized or avoided altogether, which is believed to be advantageous when particles are used that display poor hemocompatibility.

The membranes of the invention comprise at least one polymer selected from the group consisting of polysulfone, polyethersulfone, polyphenylenesulfone, polyarylethersulfone, polyamide, polyetherimide, polyimide, polyethylene-co-vinyl alcohol, polyethylene-co-vinyl acetate, cellulose acetate, cellulose triacetate, polyvinylidene fluoride, polyvinylchloride, polyacrylonitrile, polyurethane, polyether ether ketone, and polyacrylic acid. In preferred embodiments, the polymer is polyethersulfone (PES).

In some embodiments, the polymer concentration in the polymer solution from which the membrane is prepared is in a range of from 3 to 50% by weight as compared to the total weight of the solution, preferably in a range of from 5 to 35%, most preferably in a range of from 10 to 20 wt. %.

In some embodiments, the membrane comprises a polymer having a molecular weight in a range of from 1,000 to 1,000,000 grams per mole (g/mol), preferably in a range of from 30,000 to 500,000 g/mol.

The membranes of the invention further comprises at least one hydrophilic additive selected from the group consisting of polyvinylpyrrolidone, polyethylene glycol, dextran, glycerol, diethylene glycol, octanol, oxalic acid, maleic acid, tartaric acid, fumaric acid, lithium chloride, and calcium chloride. Preferably, the hydrophilic additive is polyvinylpyrrolidone. The polyvinylpyrrolidone preferably has a molecular weight in a range of from 2,500 to 2,500,000 g/mol, more preferably in a range of from 2,500 to 500,000 g/mol.

The membrane preferably comprises a hydrophilic additive in an amount in a range of from 0.01 to 50 wt. % as compared to the total weight of the membrane, more preferably in a range of from 0.5 to 10 wt. %.

Without wishing to be bound by theory, it is believed that the addition of the hydrophilic additive to the membrane helps to tailor the membrane morphology, improves the membrane water transport, decreases membrane fouling, increases the hemocompatibility of the membrane, or a combination thereof.

In particularly favorable embodiments, the membrane comprises polyethersulfone and polyvinylpyrrolidone.

The membranes of the invention preferably have a molecular weight cut off in a range of from 0.5 to 100 kilodaltons (kDa), more preferably in a range of from 5 to 30 kDa.

In some embodiments, the membranes of the invention have an average pore size in a range of from 1 to 50 nm, most preferably 1 to 10 nm.

The membranes of the invention preferably have a surface-to-volume ratio of at least 50 reciprocal centimeters ($cm^{-1}$), more preferably at least 100 $cm^{-1}$.

The membranes of the invention are preferably able to endure a maximal flow rate of blood in a range of from 100 to 600 milliliters per minute (mL/min), most preferably 300 to 500 mL/min.

The membranes of the invention are preferably able to endure a maximal flow rate of dialysate in a range of from 300 to 1000 milliliters per minute (mL/min), most preferably 500 to 800 mL/min.

The membranes of the invention preferably have an ultrafiltration coefficient $K_{uf}$ in a range of from 2 to 100 milliliters per squared meters per hour per millimeters of mercury (mL $m^{-2}$ $h^{-1}$ $mmHg^{-1}$), most preferably 5-40 $m^{-2}$ $h^{-1}$ $mmHg^{-1}$.

The membranes of the invention preferably have a swelling degree in a range of from 1 to 5%, most preferably 2%.

In some embodiments, the membrane comprising the sorbent particles has a maximal removal capacity of indoxyl sulfate (IS) at 4 hours in a range of from 100 to 2000 mg/m$^2$, most preferably 300 to 1000 mg/m$^2$.

In some embodiments, the membrane comprising the sorbent particles has a maximal removal capacity of hippuric acid (HA) at 4 hours in a range of from 500 to 8000 mg/m$^2$, most preferably 2000 to 5000 mg/m$^2$.

In some embodiments, the membrane comprising the sorbent particles has a maximal removal capacity of p-cresylsulfate (pCS) at 4 hours in a range of from 100 to 2000 mg/m$^2$, most preferably 300 to 1000 mg/m$^2$.

In some embodiments, the membrane comprising the sorbent particles has a maximal removal capacity of creatinine at 4 hours in a range of from 1000 to 6000 mg/m$^2$, most preferably 2000 to 4000 mg/m$^2$. In some embodiments, the membrane comprising the sorbent particles has a maximal removal capacity of endotoxins from dialysate at 4 hours in a range of from $0.2 \cdot 10^6$ to $100 \cdot 10^6$ EU/m$^2$, most preferably $0.4 \cdot 10^6$ to $55 \cdot 10^6$ EU/m$^2$. These values may depend on the bacterial source of the endotoxins and/or on the endotoxin concentration in the dialysate.

The skilled person is aware of methods to prepare membranes, and in particular mixed matrix membranes, more particularly dual-layer mixed matrix membranes. An overview of membrane preparation techniques is for example given by Ladewig and Al-Shaeli in *Fundamentals of Membrane Bioreactors—Chapter 2: Fundamentals of Membrane Processes*, Springer 2017, pages 13-37. A non-limiting example of a membrane preparation method is phase inversion. Phase inversion can be further specified in different techniques such as precipitation by solvent evaporation, precipitation by controlled evaporation, thermal precipitation, precipitation from the vapor phase, and immersion precipitation. The latter is also known as nonsolvent induced phase inversion.

The membrane according to the invention may be in a form selected from the group consisting of hollow fiber membranes and flat sheet membranes. In preferred embodiments, the membrane is a hollow fiber membrane.

The compositions of the invention are for use in the simultaneous removal of endotoxins from dialysate and uremic solutes from blood during the treatment of patients, wherein the treatment is selected from the group consisting of hemodialysis and hemodiafiltration.

When the treatment is hemodialysis, the duration of treatment is preferably in a range of from 1 to 36 hours, more preferably in a range of from 1 to 24 hours. Most preferably, the duration of treatment is 4 hours when the treatment is hemodialysis.

When the treatment is hemodiafiltration, the duration of treatment is preferably in a range of from 1 to 36 hours, more preferably in a range of from 1 to 24 hours. Most preferably, the duration of treatment is 4 hours when the treatment is hemodiafiltration.

In some embodiments, the dialysate comprises endotoxins at a concentration of at most 2000 EU/mL at the point in time when the dialysate is first brought into contact with the membrane of the invention. Preferably, the endotoxin concentration at the point in time when the dialysate is first brought into contact with the membrane of the invention is at most 1500 EU/mL, more preferably at most 1000 EU/mL, even more preferably at most 750 EU/mL, at most 500 EU/mL, at most 400 EU/mL, at most 300 EU/mL, at most 200 EU/mL, at most 100 EU/mL, at most 90 EU/mL, at most 80 EU/mL, at most 70 EU/mL, at most 60 EU/mL, at most 50 EU/mL, at most 40 EU/mL, at most 30 EU/mL, at most 25 EU/mL, at most 20 EU/mL, at most 15 EU/mL, at most 10 EU/mL, at most 9 EU/mL, at most 8 EU/mL, at most 7 EU/mL, at most 6 EU/mL, at most 5 EU/mL, at most 4 EU/mL, at most 3 EU/mL, at most 2 EU/mL or at most 1 EU/mL.

As explained above, different standards for the maximum level of endotoxins in dialysate may apply, and these may differ between dialysate for use in hemodialysis or hemodiafiltration.

It will be understood that the endotoxin concentration as mentioned herein relates to said concentration in the dialysate, and does not define a component of the composition of the invention.

Methods to measure a concentration of endotoxins are known to the skilled person. Preferably, the determination of the concentration of endotoxins end-point chromogenic Limulus Amebocyte Lysate (LAL) assay is performed, preferably with a detection limit of 0.015 EU/mL, and preferably according to the manufacturer's guidelines.

When the treatment is hemodialysis, the dialysate comprises endotoxins at a concentration of at least 0.03 EU/mL at the point in time when the dialysate is first brought into contact with the membrane of the invention. In some embodiments, when the treatment is hemodialysis the endotoxin concentration in the dialysate at the point in time when the dialysate is first brought into contact with the membrane of the invention is at least 0.50 EU/mL, at least 0.25 EU/mL, at least 0.125 EU/mL, or at least 0.05 EU/mL.

In some embodiments, when the treatment is hemodialysis, the dialysate comprises endotoxins at a concentration of at most 0.25 EU/mL after first contact with the membrane of the invention. In some embodiments, when the treatment is hemodialysis the endotoxin concentration in the dialysate after first contact with the membrane of the invention is at most 0.50 EU/mL, at most 0.125 EU/mL, at most 0.05 EU/mL or at most 0.03 EU/mL.

When the treatment is hemodiafiltration, the dialysate comprises endotoxins at a concentration of at least 0.03 EU/mL at the point in time when the dialysate is first brought into contact with the membrane of the invention. In some embodiments, when the treatment is hemodiafiltration the endotoxin concentration in the dialysate at the point in time when the dialysate is first brought into contact with the membrane of the invention is at least 0.50 EU/mL, at least 0.25 EU/mL, at least 0.125 EU/mL, or at least 0.05 EU/mL.

In some embodiments, when the treatment is hemodiafiltration, the dialysate comprises endotoxins at a concentration of at most 0.25 EU/mL after first contact with the membrane of the invention. In some embodiments, when the treatment is hemodiafiltration the endotoxin concentration in the dialysate after first contact with the membrane of the invention is at most 0.50 EU/mL, at most 0.125 EU/mL, at most 0.05 EU/mL or at most 0.03 EU/mL.

In preferred embodiments, during treatment no significant transfer of endotoxins from the dialysate to the blood occurs. Preferably, no significant levels of endotoxins are observed in the blood of the patient during treatment.

The skilled person is aware of other requirements for the composition of the dialysate such as type of buffer, concentration of buffer, concentration of glucose, concentration of ions, and the like.

Uremic solutes are herein defined as toxins that are present in the blood of a patient. These toxins may be bound to proteins in the blood. Non-limiting examples of uremic solutes are urea, creatinine, cyanate, polyols (e.g. myoinositol), phenols, so-called "middle molecules", $\beta_2$-microglobulin, indoxyl sulfate, p-cresyl sulfate, and hippuric acid.

The skilled person is aware of methods to measure the concentration of one or more uremic solutes. Preferably, the concentration of a uremic solute, preferably indoxyl sulfate (IS) and/or hippuric acid (HA), are analyzed using reverse-phase high-performance liquid chromatography. Preferably, the concentration of IS is measured by fluorescence ($\lambda_{ex}$=272 nm, $\lambda_{em}$=374 nm). Preferably, the concentration of HA is measured by UV detection at 245 nm. In a preferred embodiment, before IS and HA quantification, plasma and dialysate samples are deproteinized via heat treatment, preferably at 95° C. for 30 minutes, and subsequently filtered, preferably through a 30 kDa filter.

It will be understood that the membrane of the invention may be incorporated into a dialyzer unit. Preferably, the dialyzer unit is portable.

It will be understood that herein, dialysate and dialysis fluid are used interchangeably.

The invention is hereinafter illustrated with reference to the following, non-limiting, examples.

EXAMPLES

Example 1: Preparation of Mixed Matrix Membrane

The dual layer MMM was produced by dry-wet spinning technique as described in Pavlenko et al., *Scientific Reports* volume 6, Article number: 34429 (2016). The polymer dope solution for the inner layer and for the outer layer were prepared by dissolving polyethersulfone (PES) and polyvinylpyrrolidone (PVP) in N-methyl-2-pyrrolidone (NMP). Active carbon (AC) was added to the dope solution of the outer layer. The concentrations of PES, PVP and AC used are specified in Table 1. Once prepared, the polymer solutions were transferred into stainless-steel syringes and left to degas overnight. Afterwards, the polymer dope solutions were connected to high-pressure syringe pumps and to a designed spinneret for double layer hollow fibers together with the bore solution (ultra-pure water). The air-gap between the spinneret and the coagulation bath was adjusted to 10 cm.

TABLE 1

Spinning conditions of dual layer MMM hollow fiber.

| | |
|---|---|
| Inner layer composition (PES/PVP) | 15/7 wt. % |
| Outer layer composition (PES/PVP/AC) | 14/1.4/60 wt. % |
| Inner layer pumping speed | 0.4 mL/min |
| Outer layer pumping speed | 1.6 mL/min |
| Bore liquid | Ultra-pure water |
| Bore liquid pumping speed | 1.2 mL/min |
| Air gap | 10 cm |
| Collecting wheel speed | 8.3 m/min |

Example 2: Characterization of the Mixed Matrix Membrane

The mixed matrix membrane prepared in Example 1 was characterized by scanning electron microscopy (SEM, JEOL JSM-IT 100, Tokyo, Japan, results are shown in FIG. 1). For the imaging of the cross-sections, the membranes were dried in air and fractured in liquid nitrogen. Prior to SEM imaging, the samples were gold sputtered using the Cressington 108 auto sputter (Cressington Scientific Instruments, Watford, UK).

The inner layer (lumen/blood side of the fiber) is particle-free and the outer layer contains the AC particles. In the outer layer, the AC is well-dispersed in the polymer matrix. In order to have a low mass transfer resistance and a high adsorption capacity, the double layer MMM has a thinner inner layer compared to the outer MMM layer. Moreover, the two layers are well interconnected. The single layer PES/PVP hollow fiber (FIGS. 1C and 1D) was prepared using the same spinning conditions and polymer concentrations as for the inner layer of the dual layer MMM (Example 1, Table 1). The single layer PES/PVP hollow fiber is particle-free.

Figure 2:
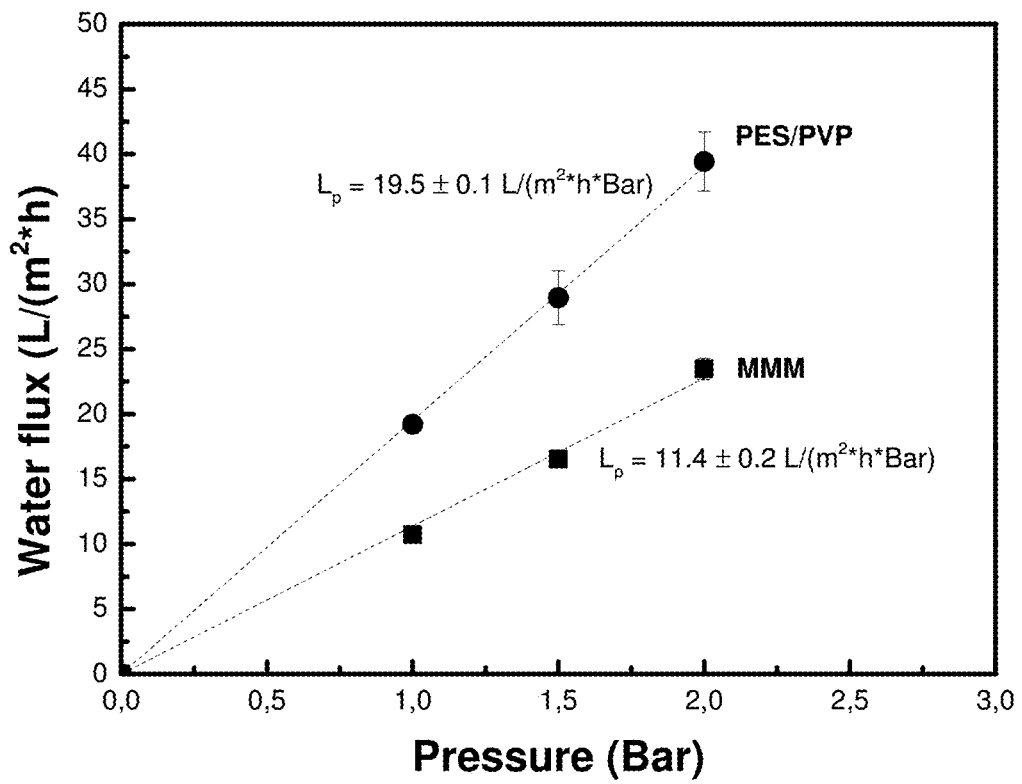
FIG. 2 depicts the results of the clean water flux through the dual layer MMM and a single layer PES/PVP hollow fiber without particles.

The mixed matrix membrane prepared in Example 1 was also characterized in terms of clean water transport (FIG. 2) and compared to PES/PVP hollow fiber without sorbent particles. Prior to the water transport experiment the membranes were cyclically flushed with NaOH 1M (30 minutes), HCl 1M (30 minutes) and EtOH 95% (30 minutes). Between each cleaning solution agent and at the end, the hollow fibers were flushed with endotoxin-free water (15 minutes). Then, the membrane modules were flushed for 30 minutes with EtOH and pre-compacted with ultra-pure water at a trans-membrane pressure (TMP) of 2 Bar for 30 minutes. Afterwards, the amount of permeated water was measured over time at transmembrane pressures of 1, 1.5 and 2 Bar. The resulting water permeance was calculated as the slope of the linear fit of the flux (L/($m^2$ h)) versus the TMP (Bar). The water permeance of the dual layer MMM is in the low ultrafiltration range having a water permeance equal to 11.4±0.2 L/($m^2$ hBar). The water permeance of the PES/PVP hollow fiber was 19.5±0.1 L/($m^2$ hBar).

Other characteristics of the MMM and the PES/PVP hollow fiber are listed in Table 2.

TABLE 2

Dimensions of MMM and PES/PVP hollow fiber.
The data are expressed as mean ± standard deviation.

| | MMM | PES/PVP |
|---|---|---|
| Outer diameter (μm) | 519 ± 6 | 487 ± 7 |
| Inner diameter (μm) | 306 ± 2 | 402 ± 5 |
| Inner layer thickness (μm) | 46 ± 7 | 44 ± 4 |
| Outer layer thickness (μm) | 64 ± 4 | — |

Example 3: Simultaneous Removal of Endotoxins from Dialysate and Protein-Bound Uremic Solutes from Human Plasma The combined removal of endotoxins from the dialysate and protein-bound uremic solutes from human plasma by the dual layer MMM was investigated performing experiments in diffusion mode (no trans-membrane pressure) and in counter-current configuration using a dedicated set up (Convergence, The Netherlands).

All the glassware, tubing and membranes used in Examples 3 and 4 were subjected to a depyrogenation treatment. The glassware was cyclically washed for 15 min with 1 M NaOH (Sigma-Aldrich Chemie GmbH, Munchen, Germany), 1 M HCl (Sigma-Aldrich Chemie GmbH, Munchen, Germany) and 95% EtOH (Boom B V, Meppel, The Netherlands) in an ultrasonic bath. Rinsing with endo-toxin-free water (Charles River Microbial Solutions, Dublin, Ireland) was performed in between each solution treatment and at the end. Afterwards, the cleaned glassware was left in oven at 180° C. for at least 3.5 h and stored in closed containers at −20° C. till use. The membranes and the tubing were cyclically flushed for 30 min with 1 M NaOH, 1 M HCl and 95% EtOH. Between each cleaning solution agent and at the end the membranes were flushed with endotoxinfree water (for 15 min). Prior to endotoxins adsorption experiments, the water of the last cleaning step (for 30 min) was analyzed to confirm that no endotoxins were present in the membranes, tubing or module. After the cleaning treatment, the fibers were immediately used to avoid contamination.

Figure 3:
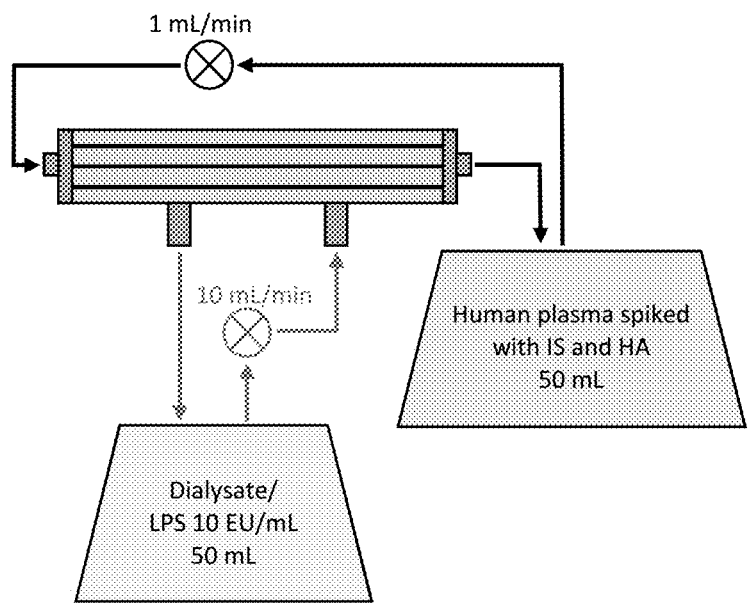
FIG. 3 shows the experimental set-up for the combined removal of LPS and indoxyl sulfate (IS) and hippuric acid (HA) protein-bound uremic solutes as used in Example 3.

After depyrogenation of the membrane modules, glassware, and of the tubing system, 50 mL human plasma (obtained by healthy donors in compliance with local ethical guidelines—Sanquin, Amsterdam, The Netherlands) spiked with indoxyl sulfate (Sigma-Aldrich Chemie GmbH, Schnelldorf, Germany) (IS, 37±3 mg/L) and hippuric acid (Sigma-Aldrich Chemie GmbH, Schnelldorf, Germany) (HA, 109±9 mg/L) was recirculated at a flow rate of 1 mL/min in the blood compartment (i.e. the lumen of the fibers). 50 mL of dialysate challenged with lipopolysaccharides (LPS; from *Pseudomonas aeruginosa* 10, Sigma-Aldrich Chemie GmbH, Schnelldorf, Germany)) (10.4±1.4 EU/mL) was recirculated at a flow rate of 10 mL/min in the dialysate compartment (i.e. on the outer side of the fiber) (FIG. 3). Membrane modules composed of 3 fibers with an effective length of 10 cm each, and with a total surface area of 2.6 cm$^2$ for the MMM and 3.5 cm$^2$ for the PES/PVP control, were used. As controls, the diffusion experiments were performed also by recirculating dialysis fluid not contaminated with LPS and healthy plasma not spiked with uremic solutes, using either the MMM or the control PES/PVP hollow fiber. The experiments were run for 4 hours and samples were taken every hour from the blood and dialysate compartments for quantification of LPS, IS, and HA. Experiments were performed in triplicate, except for IS and HA removal using PES/PVP hollow fiber where experiments were performed in duplicate. All removal results were normalized to the internal surface areas of the fiber modules.

For the quantification of LPS, end-point chromogenic Limulus Amebocyte Lysate (LAL) assay (Charles River Microbial Solutions, Dublin, Ireland), with detection limit of 0.015 EU/mL, was performed according to the manufacturer's guidelines. The concentration of IS and HA were analyzed using reverse-phase high-performance liquid chromatography (HPLC, JASCO, Tokyo, Japan). The concentration of IS was measured by fluorescence ($\lambda_{ex}$=272 nm, $\lambda_{em}$=374 nm). The concentration of HA was measured by UV detection at 245 nm. Before IS and HA quantification, plasma and dialysate samples were deproteinized via heat treatment at 95° C. for 30 minutes and subsequently filtered through a 30 kDa filter (AmiconUltracel-30 K, Sigma Aldricht Chemie GmbH, Schnelldorf, Germany).

All the data are presented as mean±SD (standard deviation). Statistical analyses were performed using GraphPad Prism version 5.02 (GraphPad Prism Software, La Jolla, Calif., USA). Statistical differences for the experiments, i.e. water transport and combined removal of LPS from dialysate and uremic solutes from human plasma were determined using unpaired students' t test. Quantitative real-time PCR results were analyzed for statistical differences using one-way analysis of variance (ANOVA) with Dunnett post-hoc test. Differences were considered significant at $p<0.05$.

Figure 4:
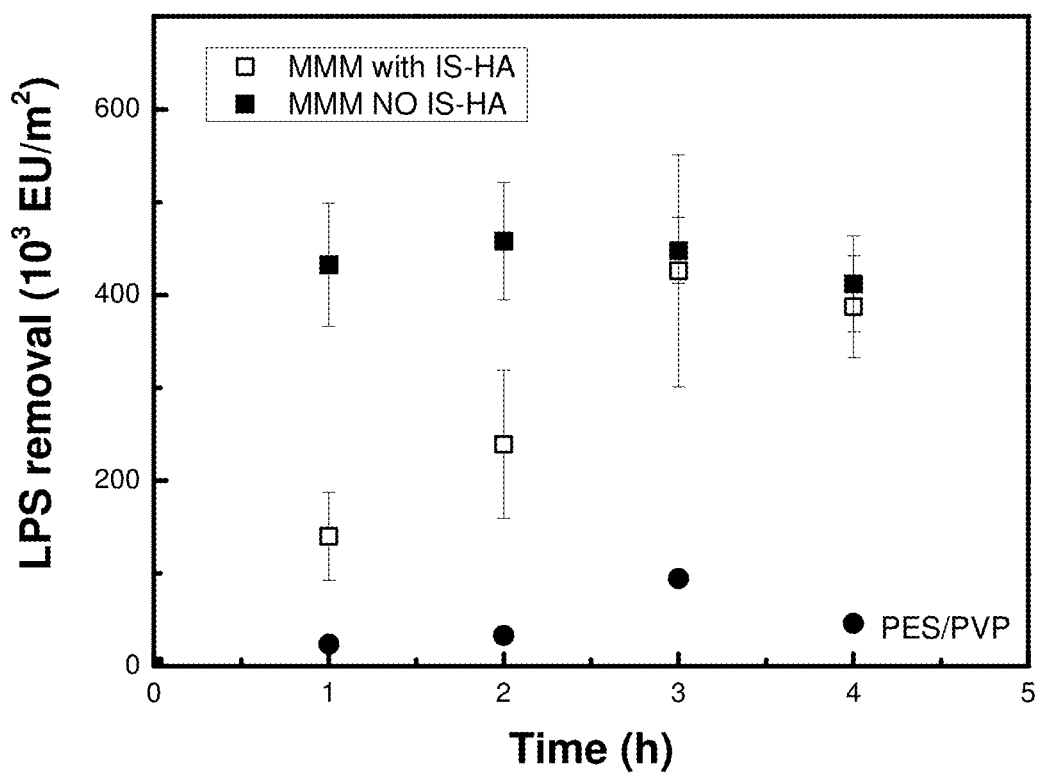
FIG. 4 depicts the results of an experiment wherein the combined diffusion of LPS (*P. aeruginosa*) and protein-bound uremic solutes (IS and HA) is measured using MMM. The LPS removal by the MMM in the presence or absence of protein-bound uremic solutes in human plasma is compared. The removal of LPS by the single layer PES/PVP membrane, without sorbent particles, is also shown.

In FIG. 4, the LPS removal by the MMM in the presence and absence of uremic solutes in human plasma is compared. The removal of LPS using the single layer PES/PVP hollow fiber is also shown. Although during the first 2 hours the kinetics of the LPS removal is slower in the presence of IS and HA in human plasma, the MMM is able to remove in both cases approximately 400000 EU/m$^2$ at 4 h. As a result, we can conclude that the total LPS removal by the MMM is not affected by the adsorption of protein-bound toxins on the AC. In both cases LPS was not detected in the blood plasma compartment, meaning that the removal was entirely due to adsorption on the MMM and that the membrane acts as a safe barrier to avoid transport of endotoxins to the blood side. The removal of LPS by the PES/PVP hollow fiber is 46000 EU/m$^2$ at 4 h, which is nearly 10 times lower compared to the MMM.

Figure 5:
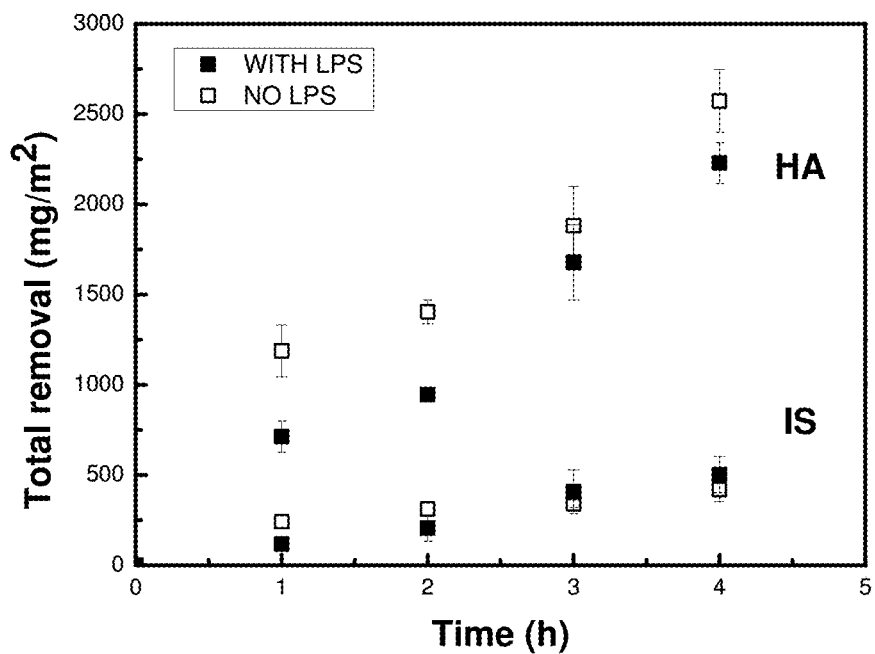
FIG. 5 depicts the results of an experiment wherein the combined diffusion of LPS (*P. aeruginosa*) and protein-bound uremic solutes (IS and HA) using MMM is measured. The IS and HA removal from human plasma by the MMM in the presence or absence of LPS in the dialysate side, is compared.

Also, the removal of HA and IS uremic solutes is not affected by the simultaneous adsorption of LPS on the AC of the dual layer MMM (FIG. 5). Only the HA removal is slightly lower at 4 hours when the dialysate is challenged with LPS, but it is still dramatically higher (around 2230 mg/m$^2$) compared to PES/PVP hollow fiber (around 1540 mg/m$^2$). Similarly, the IS total removal is remarkably higher when MMM is used compared to the single layer PES/PVP hollow fiber thanks to the presence of AC.

Figure 6:
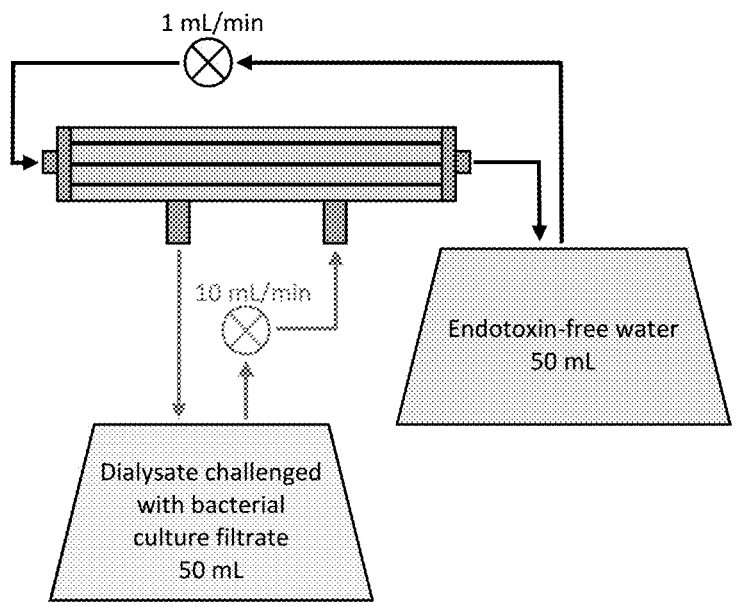
FIG. 6 shows the experimental set-up for the in-vitro dialysis experiment performed using dialysate challenged with bacterial culture filtrate.

Example 4: In Vitro Dialysis Simulation Using Bacterial Culture Filtrates as Challenge Material For the preparation of the bacterial filtrate, *Pseudomonas aeruginosa* ATCC 27853 and *Stenotrophomonas maltophilia* ATCC 13637 were cultured at 37° C. in tryptic soy broth until the log phase of growth. The bacteria were subsequently killed via ultrasonication and then filtered using decreasing pore size for further fractionation. Equal volumes of the bacterial filtrates were then pooled together and diluted using endotoxin-free dialysate to a final concentration of endotoxins of 50 EU/mL. In vitro dialysis was performed in diffusion mode (no trans-membrane pressure) and in counter-current configuration using a dedicated set up (Convergence, The Netherlands). In the lumen of the fibers endotoxin-free water was recirculated at a flow rate of 1 mL/min. On the outside of the fibers dialysate challenged with the bacterial filtrate was recirculated at a flow rate of 10 mL/min (FIG. 6). Membrane modules composed of 3 fibers with an effective length of 10 cm each were used. The experiments (three replicates) were run for 4 hours and samples were taken every hour from the blood and dialysate compartments. The samples were freeze-dried and resuspended in fresh cell culture media (RPMI 1460).

Figure 7:
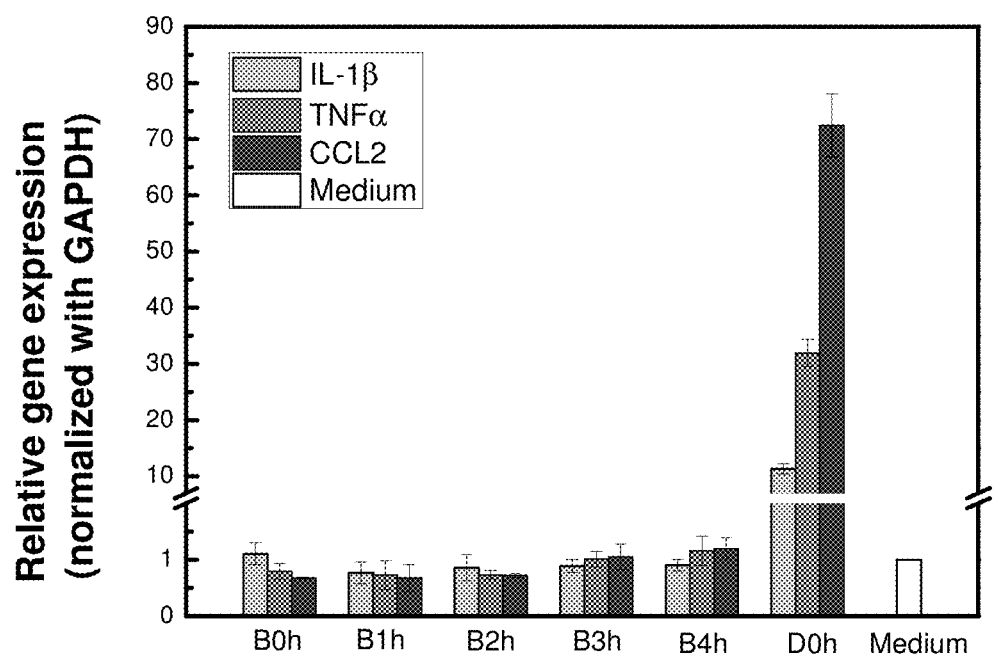
FIG. 7 illustrates the IL-1$\beta$, TNF-$\alpha$ and CCL2 quantitative gene expressions in THP-1 cells (human monocytes cell line) after 24 hours incubation with samples collected from the in-vitro dialysis experiment performed using the MMM and dialysate challenged with bacterial culture filtrate. On the x-axis, the dialysate challenged with bacterial culture filtrate is denoted with D0$h$, the samples from the blood compartment at the different time points with B0$h$, B1$h$, B2$h$, B3$h$, and B4$h$, and the negative control with medium.

THP-1 cells (human monocytes cell line) were incubated with the samples for 24 hours before lysis. Total RNA was isolated (GenElute Total RNA Miniprep Kit—Sigma) and 0.5 μg was reverse-transcribed using iScript cDNA Synthesis Kit (Bio-Rad). Real-time PCR was performed using 2× SensiMix SYBR and Fluorescein Kit (Bioline, QT615-05) and 20 ng cDNA. Cycle threshold (Ct) values were normalized to reference gene GAPDH and fold changes in expression were calculated using the 2−ΔΔCt method. To investigate if bacterial material moved from the dialysate compartment to the blood compartment, the expression of genes related to inflammation (IL-1β, TNFα, CCL2) was analyzed. In FIG. 7 it is possible to observe the strong upregulation of IL-1β, TNFα and CCL2 for the cells incubated with the dialysate challenged with bacterial culture filtrate (D0*h* in FIG. 7), proof of the pronounced ability of the dialysate to trigger inflammation. No significant difference of IL-1β, TNFα and CCL2 gene expression was observed for the samples from the blood compartment at the different time points (B0*h*, B1*h*, B2*h*, B3*h*, B4*h*) and the negative control (medium). These data prove that material from the bacterial culture filtrate is not able to reach the blood compartment due to adsorption by the MMM which acts a barrier able to avoid the transport of pyrogen materials to the blood.

The invention claimed is:

1. A method of hemodialysis or hemodiafiltration treatment of patients, wherein said method comprises the step of
simultaneously removing endotoxins from dialysate and uremic solutes from blood by contacting said dialysate and said blood with a composition comprising sorbent particles;
wherein said particles are embedded into a membrane, said membrane comprising at least one polymer selected from the group consisting of polysulfone, polyethersulfone, polyphenylenesulfone, polyarylethersulfone, polyamide, polyetherimide, polyimide, polyethylene-co-vinyl alcohol, polyethylene-co-vinyl acetate, cellulose acetate, cellulose triacetate, polyvinylidene fluoride, polyvinylchloride, polyacrylonitrile, polyurethane, polyether ether ketone, and polyacrylic acid;
wherein said membrane further comprises at least one hydrophilic additive selected from the group consisting of polyvinylpyrrolidone, polyethylene glycol, dextran, glycerol, diethylene glycol, octanol, oxalic acid, maleic acid, tartaric acid, fumaric acid, lithium chloride, and calcium chloride;
whereby in said treatment the dialysate comprises endotoxins at a concentration of at least 0.03 EU/mL when the dialysate is first brought into contact with said membrane.

2. The method according to claim 1, wherein said dialysate comprises endotoxins at a concentration of at most 2000 EU/mL when the dialysate is first brought into contact with said membrane.

3. The method according to claim 1, wherein the sorbent particles are selected from the group consisting of activated carbon particles, ion exchange resins, unmodified silica particles, $C_2$-derivatized silica particles, $C_4$-derivatized silica particles, $C_6$-derivatized silica particles, $C_8$-derivatized silica particles, $C_{16}$-derivatized silica particles, ion exchange silica particles, zeolites, ceramic particles, porous polymeric particles, non-porous polymeric particles, molecular imprinted particles, and combinations thereof.

4. The method according to claim 1, wherein the sorbent particles are activated carbon particles.

5. The method according to claim 1, wherein the membrane comprises polyethersulfone and polyvinylpyrrolidone.

* * * * *